United States Patent [19]

Pourcelot et al.

[11] Patent Number: 4,605,009

[45] Date of Patent: Aug. 12, 1986

[54] ULTRASONIC SWEEP ECHOGRAPHY AND DISPLAY ENDOSCOPIC PROBE

[75] Inventors: Léandre Pourcelot, Saint Avertin; Gérard Fleury, Fondettes Par Luynes; Marceau Berson, Joue les Tours, all of France

[73] Assignee: Universite Francois Rabelais, Tours, France

[21] Appl. No.: 597,054

[22] Filed: Apr. 5, 1984

[30] Foreign Application Priority Data

Apr. 6, 1983 [FR] France .................................. 83 05610

[51] Int. Cl.[4] .............................................. A61B 10/00
[52] U.S. Cl. ......................................... 128/660; 128/6
[58] Field of Search ................................. 128/660–663, 128/4, 6

[56] References Cited

U.S. PATENT DOCUMENTS

| | | | |
|---|---|---|---|
| 3,938,502 | 2/1976 | Bom | 128/660 |
| 4,327,738 | 5/1982 | Green et al. | 128/660 |
| 4,344,327 | 8/1982 | Yoshikawa et al. | 128/661 X |
| 4,409,982 | 10/1982 | Plesset et al. | 128/660 |
| 4,433,692 | 2/1984 | Baba | 128/660 |
| 4,462,092 | 7/1984 | Kawabuchi et al. | 128/660 X |
| 4,462,408 | 7/1984 | Silverstein et al. | 128/4 X |
| 4,494,549 | 1/1985 | Nambo et al. | 128/660 |

FOREIGN PATENT DOCUMENTS 77923  9/1982  European Pat. Off. ............ 128/660

*Primary Examiner*—Kyle L. Howell
*Assistant Examiner*—Francis J. Jaworski
*Attorney, Agent, or Firm*—Larson and Taylor

[57] ABSTRACT

The endoscopic probe, more especially for medical use, comprises a tubular member insertable in a cavity to be explored, having a flexible part ending in an endmost section able to be orientated by means of mechanical control means disposed inside the flexible section. The section carries optical illumination and image return means and an ultrasonic electro-acoustic translater. This translator comprises a fixed curved linear array of piezoelectric elements, the convexity of the curve being directed outwardly. The array is associated with an electronic circuit for energizing the elements according to a sectorial sweep sequence in an angular field overlapping with the field of view of the optical means.

8 Claims, 11 Drawing Figures

U.S. Patent  Aug. 12, 1986  Sheet 1 of 7  4,605,009
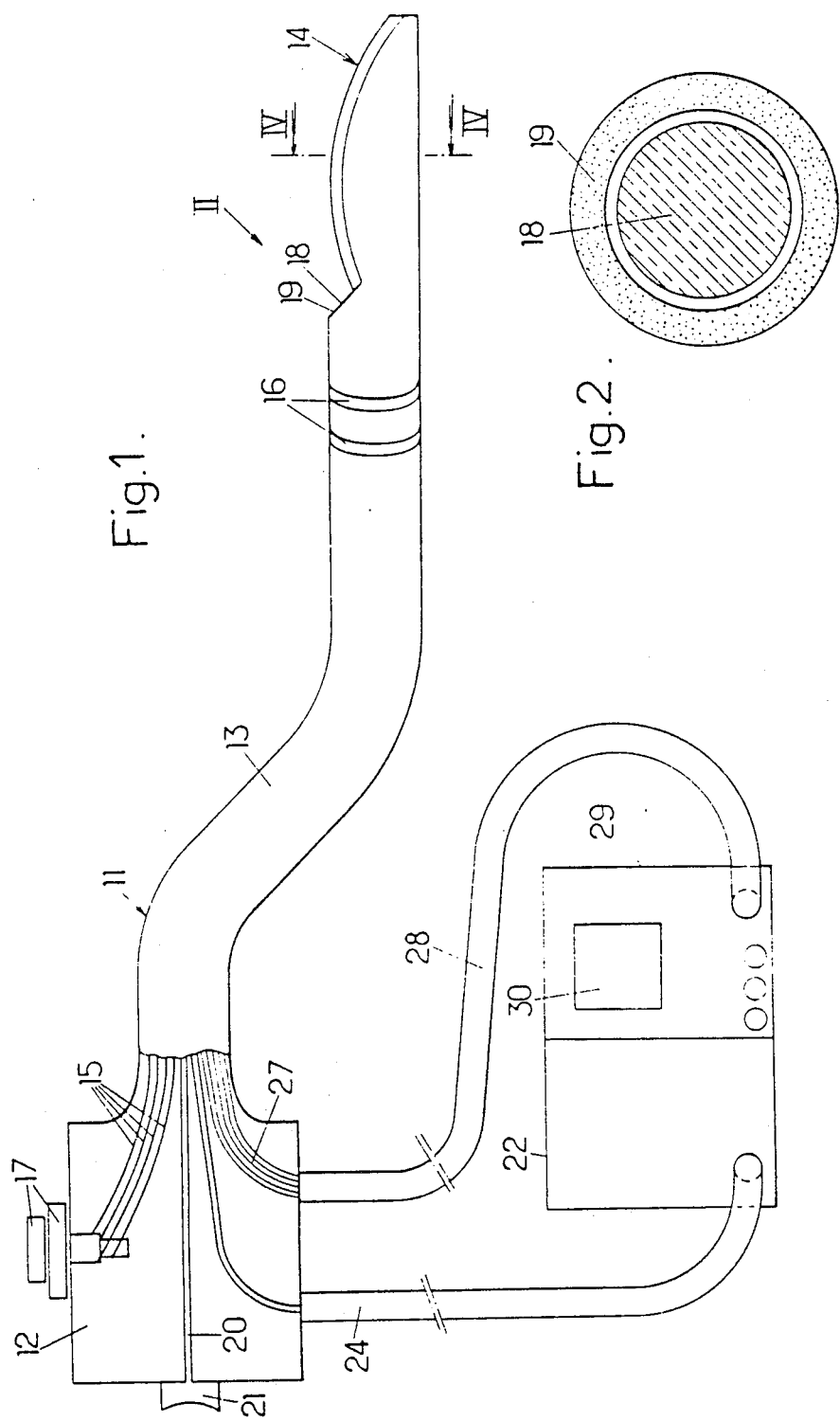

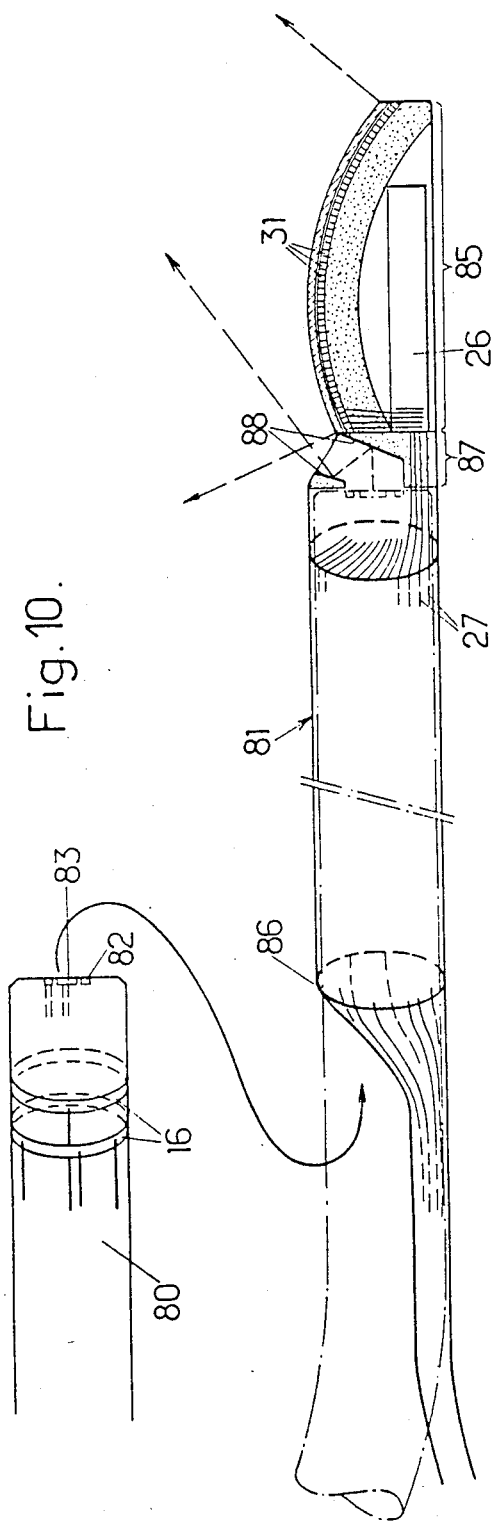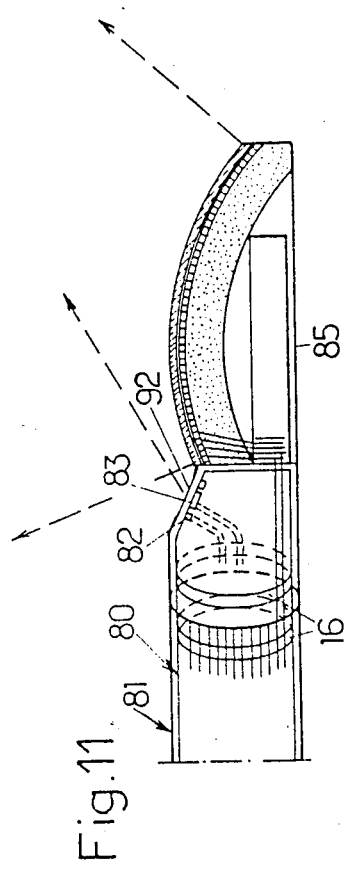

ULTRASONIC SWEEP ECHOGRAPHY AND DISPLAY ENDOSCOPIC PROBE

BACKGROUND AND SUMMARY OF THE INVENTION

The invention relates to an ultrasonic echography and display endoscopic probe and it finds a particularly important, although not exclusive application in the medical field, formed by the optical and echography observation of the internal walls of the human body, especially of the oesophagus, of the stomach and of the duodenum.

Optical endoscopes are already widely used for observing the internal walls or linings of the human body. These endoscopes are formed by a long flexible tube or pipe fixed at one end to a control box comprising members for guiding, by means of fine cables, a rigid end section of the tube. The light is transmitted from an external source to an emitter, placed in the endmost section for illuminating the wall, by means of optical fibers passing through the tube. The optical image collected by a lens situated at the side of the emitter is transmitted by optical fibers to a sighting eyepiece carried by the box.

It has already been proposed (EP-A-00 66 185) to complete such an endoscope with means for the echotomography of the tissues and organs situated behind the walls observed optically. For that, an ultrasonic transducer is implanted in the endmost section, at the side of the optical system. The two methods of exploration are complementary: the optical image allows the ultrasonic translator to be guided and located which is used for supplying the acoustic image. This latter may be of good quality if high frequencies are used, because of the small depth to be explored and because of the absence of highly absorbing tissues interposed between the translator and the organ.

The echotomography endoscope described in document EP-A-00 66 185 uses a single transducer having a mechanical sweep system for causing it ot oscillate about an axis which coincides with that of the endmost section, This technique presents, among other drawbacks, difficulties in forming the relatively moving parts and difficulties in detecting the movement of the transducer. So it is when this latter is fixed and when the orientation of the ultra-sonic beam is modified by means of a rotating mirror.

It is an object of the invention to provide an improved ultrasonic echography and display endoscopic probe. It is a more particular object to provide a probe which may have a wide acoustic angular field without using mobile parts, high resolution and a possibility of optical guiding, while keeping dimensions comparable to those of conventional probes.

To this end, an endoscopic probe according to the invention comprises a tubular member for insertion in a cavity to be explored, having a flexible part ending in an endmost section which is orientatable through mechanical control means disposed inside the flexible part, optical image return and illumination means and an ultrasonic electro-acoustic translator carried by said section, characterized in that the translator comprises a curved linear array of piezoelectric elements fixed in the section, the convexity of the curve being directed outwardly, which array is associated with an electronic circuit for energizing the element according to a sectorial sweep sequence in an angular field overlapping the field of view of the optical means.

The linear array will be generally formed by a single line of piezoelectric elements, the sectorial sweep taking place in a plane passing through the axis of the endmost section. The electronic circuit will generally comprise electric delay and/or phase shift means for providing not only an electronic sweep by energizing successive groups of elements, but also focusing of the array at a given distance. To the sectorial sweep achieved because of the convex form of the array may be added a sweep obtained by modifying the phase and/delay distribution during successive burst from the same group of piezoelectric elements, following a technique comparable to that used in phased plane arrays.

The material construction of the probe may take on very different forms depending on the application envisaged. There will be described hereafter, by way of examples, embodiments intended for the medical field, but a probe of the same kind may be used in numerous industrial fields, for exploring regions of machines or installations inaccessible without dismantling.

The invention will be better understood from reading the following description of probes which form particular embodiments thereof, given by way of non limiting examples.

SHORT DESCRIPTION OF THE DRAWINGS

FIG. 1 is a simplified diagram showing the general construction of a probe in accordance with the invention, shown in elevation and in partial section, FIG. 2 shows, on a large scale, the light emitter and the lens carried by the endmost section of the probe, seen in the direction of arrow II of FIGS. 1 and 3, FIG. 3 is a large scale view of the endmost section of the probe, shown in section through a plane passing through the plane of symmetry, FIG. 4 is a sectional view through line IV—IV of FIGS. 1 and 3, FIGS. 5, 6 and 7 are diagrams for showing acoustic sweep modes which may be used for implementing the probe, FIG. 8 is a block diagram showing one possible construction of the electronic means of the probe, FIGS. 9, 10 and 11 are diagrams showing different possible variants of construction of the endmost section of the probe.

DETAILED DESCRIPTION OF PREFERRED EMBODIMENTS

Figure 3:
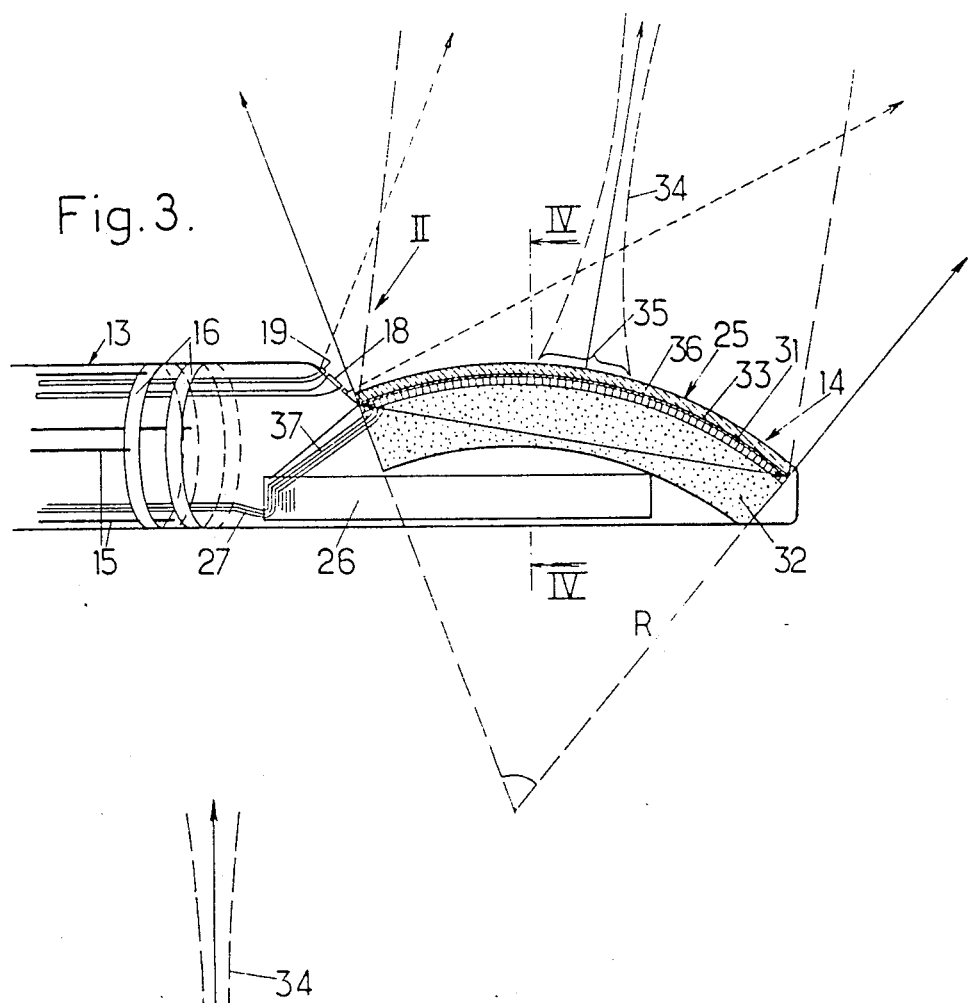

The endoscopic probe which will now be described is intended more especially for studying organs and zones of the human body to which access is difficult by external means, such as the coronary arteries, the descending aorta, the right hand heart portion, the auricles, the mediastinal masses, the pancreas, the lower bile ducts and the digestive vessels.

The probe comprises a tubular insertion member 11 connected to a control and connection box 12. The tubular member 11 has a flexible part 13 in the form of a pipe and an endmost section 14 which will be generally rigid. The flexible part contains the different electric and light conductors required for supplying the elements which are housed in the endmost section 14. It also contains fine cables 15 for guiding and orientating the end section 14, which cables are fixed two by two at their ends to rings 16 embedded in the wall of the flexible part, in the immediate vicinity of the end section.

These cables, four in number in the embodiment illustrated, are connected to control knobs 17 carried by box 12.

The optical part of the probe comprises a lens 18 and a light emitter 19 provided on the end section 14 (FIG. 2), on an oblique wall so that they are spaced apart from the wall and, as will be seen further on, present a field of view overlapping angularly with that of the echography means. The lens 18 is connected, by a flexible optical guide 20, contained in the tubular member 11, to an observation eyepiece 21. The light emitter 19 which, in the embodiment illustrated, has an annular form and surrounds lens 18, receives light coming from a source 22 through an optical fiber 23 which follows successively a tube 24 for connecting between source 22 and box 12 and tubular member 11.

The elements of the probe intended for ultrasonic exploration comprise an ultrasonic transducer 35 forming a part of the lateral wall of the rigid end section 14, a printed circuit 26 contained in this end section and miniature coaxial electric cables 27 connecting the circuit 26, through box 12 and a sheath 28 to an electronic control unit 29 having a display screen 30 and switch on and adjustment knobs (not shown).

The essential element of the ultra sonic transducer 25 is an array 31 of N electro-acoustic elements, disposed along an arc of a circle of radius R with outwardly turned convexity. As an example of the order of magnitude, a row of N=64 to 104 elements (piezoelectric material elements) disposed in a single row, along an arc of a circle of radius R=30 mm, with a chord D=30 mm, will give satisfactory results. The length of each element, which corresponds to the width of the transducer, may be 0.5 cm, the resonance frequency ranging from 5 to 10 MHz.

Figure 4:
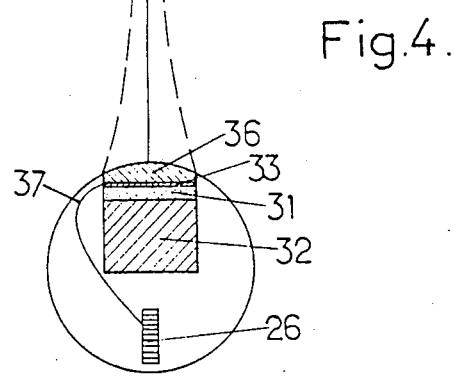

The piezoelectric elements are supported, in a known way, by a mass 32 of damping material for absorbing the energy emitted by the elements rearwardly and for rapidly absorbing the vibrations of these elements, so as to widen the pass band and optimize the axial resolution. To the front face of the piezoelectric element array is bonded a matching layer 33 having a thickness equal to a quarter of the wave length of the ultra sounds in the material which forms it. Finally, for focusing the acoustic beam 34 emitted by a group of elements 35 during the same burst, in the transverse direction with respect to the plane of symmetry, an acoustic lens 36 is bonded to the matching layer 33. Lens 36 is advantageously formed from a material in which the speed of propagation is less than the speed in the tissues (about 1500 m/s). A material will for example be chosen in which the speed of propagation is about 1000 m/s. Thus, focusing is obtained with a convex shape of the acoustic lens 36 (FIG. 4). The external face of the flat convex lens will be very little different from the curvature of the end section 14 of the endoscope, which ensures good matching and good contact with the wall of the cavity to be explored.

With the small sized printed circuit 26, the problems of direct connection of coaxial cables to the elements of array 31 are avoided. The coaxial cables are in fact connected to circuit 26, which is connected to the elements by short thin wires 37 which transport the electric pulses for energizing the piezoelectric elements and bring back the electric echo information.

Electronic scanning is achieved by energizing successive groups of piezoelectric elements of the array 31. It may be implemented using approaches which are well known, by shifting step by step the group 35 of elements participating in a same burst. Focusing of the successive beams 34 may also be obtained by well known methods, possible at a variable depth, by using a set of time delays taking into account the focusing depth to be obtained and the curvature of the array. Through the combination of electronic focusing in the scanning direction and acoustic focusing in the perpendicular plane, a high resolution may be reached and a much larger field than that with a flat strip of piezoelectric elements.

As shown in FIG. 3, the optical system and the ultrasonic echography systems are disposed with respect to each other so that the optical field and the acoustic field have a substantial overlap, whose angular extent is close to 80° in the embodiment illustrated. This overlapping has the advantage of allowing optical display of the wall to which the acoustic sensor is applied and so, verification of the conditions of the contact, promoted more over by the curved shape of the array. It should in particular be noted that the endmost section may be intimately applied against the wall by acting on the guide cables 15.

Figure 5:
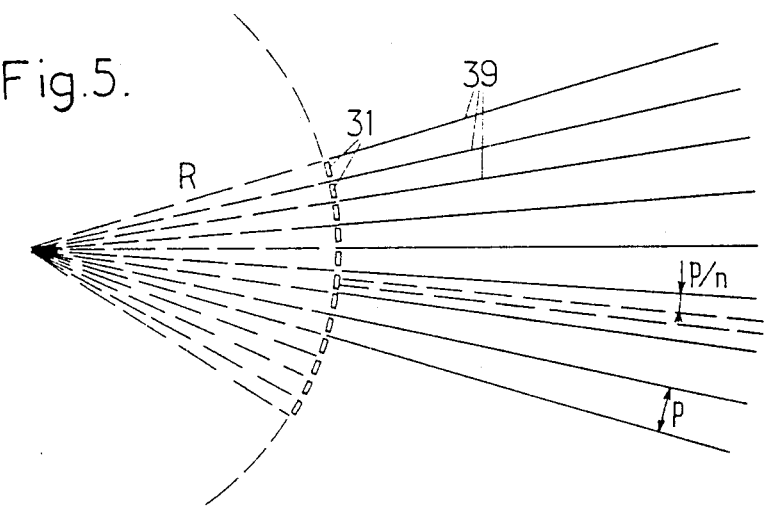
Figure 6:
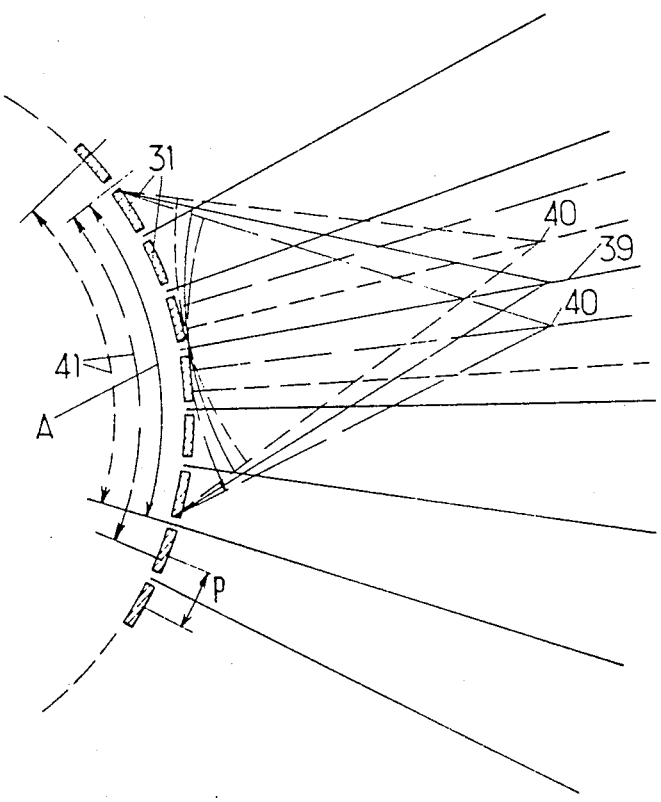

FIG. 5 shows that the sectorial sweep with a curved linear array of electro-acoustic elements results in a spacing between the successive exploration lines 39 which increases with depth and may become excessive at a distance from the transducer. To reduce this spacing, which depends on the distribution pitch p of elements 31 one solution consists in effecting several successive bursts from the same group of elements 31, but with different delay distributions for obtaining the sweep with a pitch p/n (n being equal to 2 or 3). With this process, (n−1) lines of exploration, shown with broken lines in FIG. 5, can be added between two normal adjacent exploration lines 39. As shown in FIG. 6, in the case of a group of six electroacoustic elements 31 and with n=3, a normal exploration line is obtained with a symmetrical distribution of the delays and two focusing along additional lines 40, symmetrical with respect to line 39, with delays corresponding to two fictitious apertures 41 equal to A+2p/h. This embodiment causes a division of the repetition rate of the image by n, but this reduction matters little for the usual exploration depth not exceeding 6 cm. Thus, for n=3 and a transducer 25 having an array of 100 elements 31, the rate is 60 images per second for an exploration depth of 4 cm, which is very much greater than the scintillation limit, of about 24 images per second.

Figure 7:
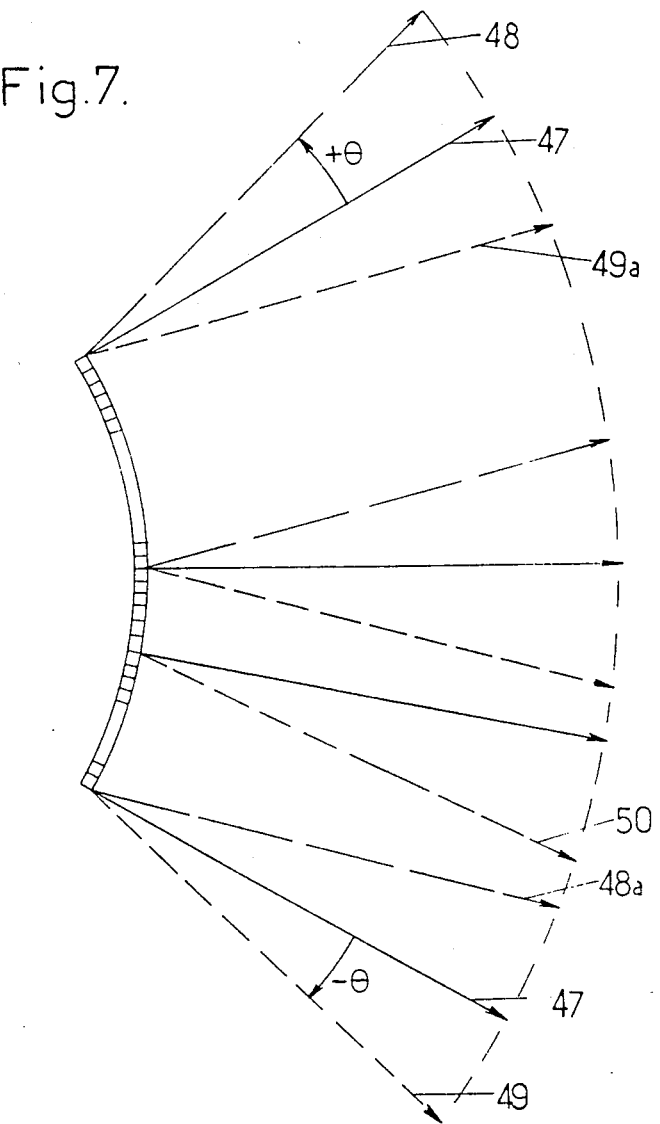

The acoustic beam may be slanted with respect to the perpendicular to the median element. FIG. 7 shows for example the endmost exploration lines 47 of the normal field, as well as the exploration limits 48 with a slant $+\theta$ and 49 with a slant $-\theta$. Electronic deflection is obtained in the same way as with a phased array, by means of a selection of delays which ensure focusing of the beam, the slant thereof and compensation for the curvature of the array.

The electronic slant of the beam may be used for obtaining focusing at the same point from several different groups of electro-acoustic elements, which allows a composite sweep to be obtained increasing the amount of information. With computer reconstruction, rounded structures may be better determined than with a single information and considerably enriches the image. With such a sweep mode, the resulting image follows from the superimposition or the combination of three images corresponding respectively to fields 47—47, 48,48a and 49a—49. The electronic sweep may of course be stopped on a given group of electro-acoustic elements for recording the movement of a structure, for example in cardiology. This same observation of a fixed zone allows flows to be determined also, for example the blood flow, by determining the Doppler effect which is particularly well suited to an oblique incidence such as the one shown at 50.

Figure 8:
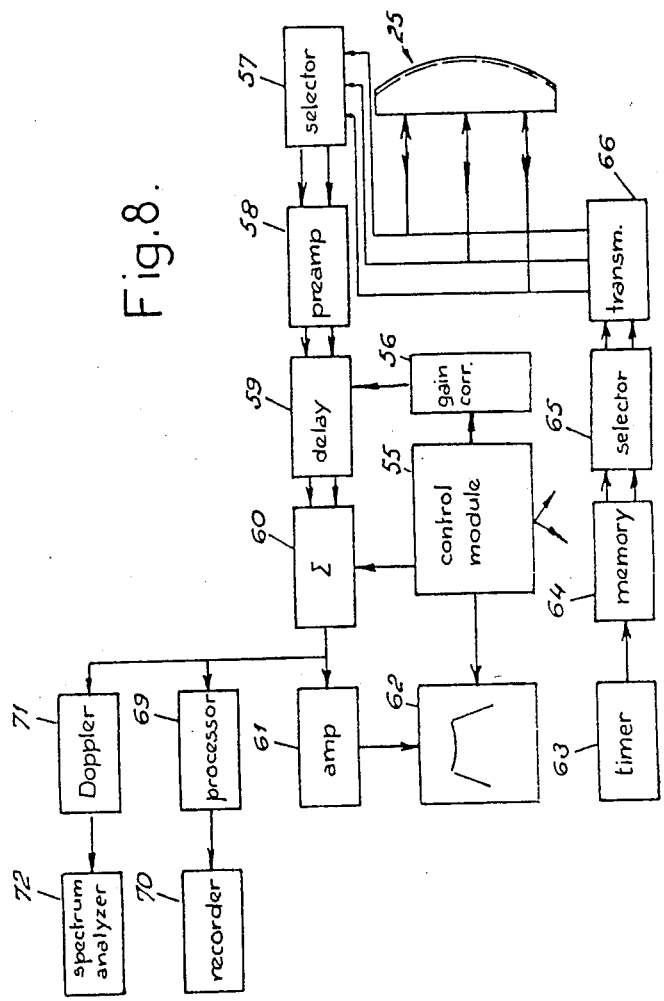

The electronic means associated with translator 25 will not be described here in detail, since they may take on numerous forms, and particularly those already well known. One possible general construction will be simply described with reference to FIG. 8. These electronic means comprise a control module 55 which controls the transmission and reception chains.

In the transmission chain, a timer 63 supplies, at regular intervals, a pulse which is transmitted to a device 64 for storing the delays corresponding to the desired focusing. Device 64 supplies the energizing signals having the different delays required for focusing and, possibly, for the formation of the additional exploration lines. The signals from device 64 are switched by selector 65 to the inputs of the transmission circuits 66 whose outputs deliver energization pulses, of sufficient level, to the x simultaneously energized electro-acoustic elements, of order n to n+x−1. This group of elements 35 emits an ultrasonic beam focused in the tissues to be studied. During the following transmission, the x signals are transmitted this time to the elements n+1 up to (n+1)+(x−1) and so on.

On reception, the procedure is reversed: the x signal supplied by the x electro-acoustic elements 35 of the group selected by the selection module 57 are transmitted to preamplifiers 58, then to a delay of phase shift system 59 and, finally, to a summing circuit 60. An adjustable gain video amplifier 61 supplies a display monitor 62 with the required analog signals. A device 56 will generally be provided for correcting the gain as a function of the exploration depth. This correction of gain may be effected by a circuit acting on the preamplifier 58 and controlled by the module 55.

The useful signal appearing at the output of summator 60 may be also directed towards a device 71 for measuring the Doppler effect, followed by a spectrum analyser 72 operating in real time and supplying the Doppler frequency spectrum. The same useful signal may be processed in a device determining the movement as a function of time 69 forstorage in a recorder 70.

Figure 9:
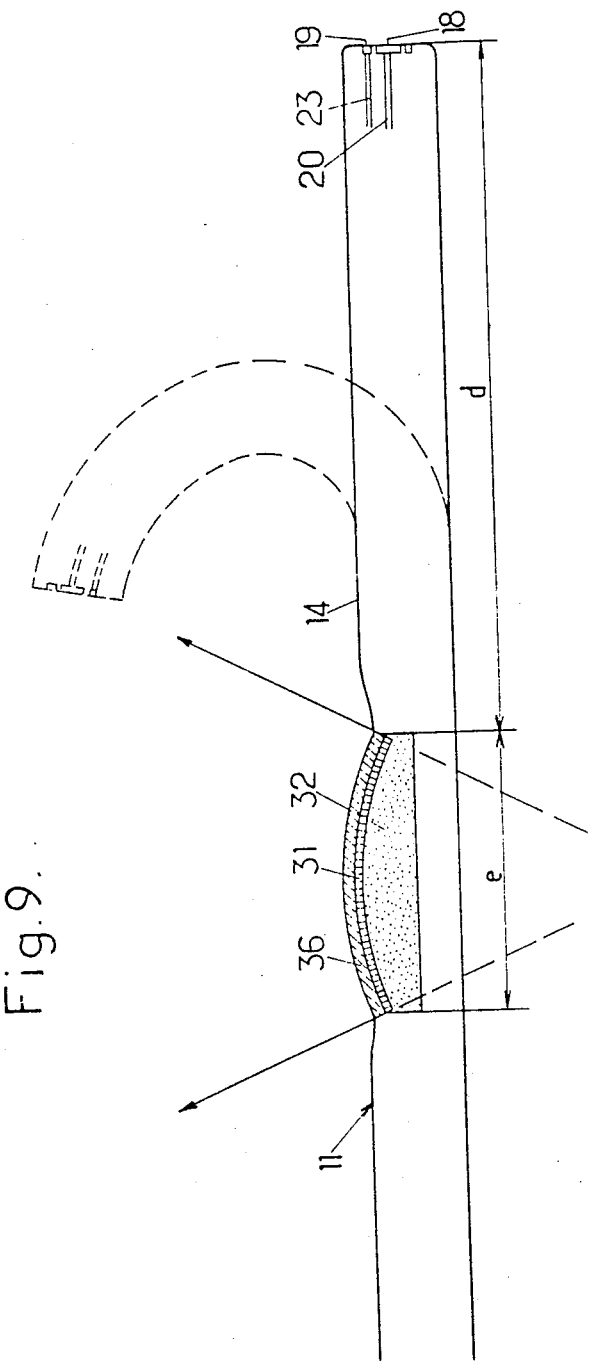

As was pointed out above, the invention is susceptible of numerous variants. FIG. 9 shows, in longitudinal section, the end part of the tubular member 11 of an endoscope with deformable endmost section. This end section has again an ultra-sonic translator formed by a curved array 31 of electro-acoustic elements covered by a lens 36 but the array is placed at distance d from the end of the tubular member 11 and the optical system, formed by lens 18 and emitter 19 on the endmost face of section 14. The section of the tubular member 11 containing the array of the electro-acoustic elements 31 is rigid, over length e. On the other hand, the part of length d, generally about 8 cm, is flexible and orientatable. The guide may thus be very flexible, the rigid part being shifted to the rear of the endmost face. Moreover, the optical display of the contact zone between the front face of the translator and the internal wall is possible when the end of the tubular member 11 is brought into the position shown with broken lines in FIG. 9.

In yet another embodiment, shown in FIG. 10, the tubular member 11 is made from two separate and interlockable modules 80 and 81. Module 80 is similar to a conventional endoscope, having a light emitter 82 and an optical lens 83 on its endmost face. Module 81 has an acoustic probe 85 of the same kind as that shown in FIG. 3. The electric cables 27 for connection between the electro-acoustic elements of the array and the associated electronic control box (not shown) are spaced apart in a thin and flexible cylindrical sheath 86 whose diameter is slightly greater than that of the endoscope 80 and whose length is at least equal to that of the tube of the endoscope.

In part 87 of module 82, which is coupled to the endmost face of the acoustic probe 85, two mirrors 88 are provided having a slant such that they guide the light from emitter 82 towards the outside through part 87. These mirrors also allow viewing of the outside through lens 83.

When it is desired to effect an echo endoscopic exploration, the endoscope 83 is first of all introduced into sheath 86 until the optical elements 82 and 83 are opposite the mirrors of part 87, as shown with a dash dot line in FIG. 10. With the guide device comprising rings 16, the echo endoscope head formed by sheath 86, probe 85 and endoscope 80 may be orientated. The additional length imposed on the rigid end portion by the addition of part 87 is small (less than a centimeter) and, at this price, an ordinary undefined endoscope may be used. Moreover, modules 80 and 81 may be used separately for conventional echographic or endoscopic examinations.

The device of which a fragment is shown in FIG. 11 forms a variant of that of FIG. 10. It comprises again an endoscopic module 80 and an acoustic module 81 formed from a sheath 86 and a probe 85. But this variant no longer has the rigid part provided with mirrors which is shown in FIG. 10. To make up for it, the optical elements 82 and 83 are no longer placed at the end of the endoscope, but laterally on a surface slanting with respect to the axis of the tube. These optical elements are thus located facing a membrane 92 when the endoscope is fully introduced into sheath 86. At the price of a slight modification of an ordinary endoscope, the complication caused by the addition of mirrors in the case of FIG. 10 is avoided.

The invention is susceptible of numerous other embodiments, considering more especially the application contemplated and it should be understood that the scope of the present patent extends to any variant remaining within the field of equivalences.

We claim:
1. An endoscopic probe system for simultaneous visual and ultrasonic imaging of internal body parts, comprising
   an endoscope insertable into a body organ and including an elongated flexible tubular member having an axis, a rigid end section having a lateral wall and connected to a distal end of said tubular member, and mechanical control means to said tubular member for adjusting the angular position of said end section with respect to said axis,
   an optical system for use in visually viewing said body organ in a predetermined field of view including lens means secured to said lateral wall of said end section, optical light carrying and image return means located within and along said flexible tubular member from said distal end to a proximal end thereof, and viewing means located outside of said flexible tubular member and connected to said optical means at said proximal end, and a ultrasonic imaging system for use in providing a display of said body organ in an angular field having an overlap with said predetermined field of view, said ultrasonic imaging system having a curved linear array of piezoelectric transducer elements fixed to said lateral wall of said end section, the convexity of said array being directed outwardly of said end section, electronic circuit means operatively associated with said transducer elements and arranged for operating said piezoelectric elements according to a predetermined sector scanning sequence for sweeping said angular field with a focussed ultrasonic beam and display means connected to said electronic means and providing a visual image of said body organ.

2. A probe system according to claim 1 wherein said linear array consists of a single line of piezoelectric elements disposed for sector scan in a plane passing through said axis of said end section.

3. A probe system according to claim 1 wherein said electronic circuit means comprises phase shift means and switching means for providing electronic scan by energizing successive groups of said transducer elements and for focusing at a predetermined distance from the array.

4. A probe system according to claim 3, wherein the electronic circuit means further comprises means for modifying the phase and/or delay distribution during successive ultrasonic bursts from a same group of piezoelectric transducer elements, so as to provide scanning both along first lines normal to the array and along additional lines at an angle with said first lines.

5. A probe according to claim 1, wherein said end section contains a printed circuit and electrical junction wires connecting said circuit to said piezoelectric elements and said tubular member contains miniature coaxial cables connecting said circuit to an electronic control box connected to a proximal end of the tubular member.

6. A probe according to claim 1 wherein said transducer means comprises a convex acoustic lens for focusing in a direction transverse to a plane of symmetry of the probe, formed from a material in which the propagation speed of the ultra sounds is less than that in biological tissues.

7. An endoscope probe for simultaneous visual and ultrasonic imaging of internal body parts, comprising:

an elongated flexible tubular member of substantially circular cross section about an axis, having a proximal end and a distal end.

a rigid end section having a front end and having a rear end secured to said distal end of said tubular member, having a shape elongated in a direction extending in the direction of of said axis in the distal end portion of said tubular member, a curved linear array of piezoelectric transducer elements extending along said end section for directing and receiving ultrasonic pulses in an angular field transverse to said direction as focussed beams, an electronic circuit board located within said end section, individually connected to said transducer elements, electric line means connected to said electronic circuit board, extending along and within said tubular member for connection to remote scanning and display means.

and light carrying and image return means including light carrying and image return lines located within and along said flexible tubular member and lens means inside a portion of a wall of said tubular member at the distal end thereof, said portion being so slanted with respect to said axis that said light carrying and image return means illuminate and provide a visual display in a sector field of view having an overlap with said angular field.

8. An endoscopic probe for simultaneous visual and ultrasonic imaging of internal body parts, comprising:

a first module having an elongated flexible sheath having a proximal and a distal end and connected at the distal end thereof to a rear end of a rigid end section for insertion into an internal body organ, a second module comprising an elongated flexible tubular member of substantially circular cross section about an axis, constructed and arranged for insertion within said sheath into abutment with said rear end, a curved linear array of piezoelectric transducer elements extending along said end section for directing and receiving ultrasonic pulses in an angular field transverse to the direction of elongation as focussed beams.

and light carrying and image return means comprising light reflecting means formed within said end section between said transducer array and said rear end, constructed and arranged for cooperation with lens means formed in an end surface of said second module for illuminating and providing an image of a sector field of view having an overlap with the angular field of said curved linear array.

* * * * *